(12) United States Patent
Dreisbach et al.

(10) Patent No.: US 10,384,987 B2
(45) Date of Patent: Aug. 20, 2019

(54) 1,3-BUTADIENE SYNTHESIS

(71) Applicant: ARLANXEO Deutschland GmbH, Dormagen (DE)

(72) Inventors: Claus Dreisbach, Leichlingen (DE); Stefan Schlenk, Kaufering (DE); Martina Hoffmann, Bergisch Gladbach (DE); Christoph Larcher, Duesseldorf (DE); Thomas Foellinger, Dormagen (DE)

(73) Assignee: ARLANXEO DEUTSCHLAND GMBH, Dormagen (DE)

( * ) Notice: Subject to any disclaimer, the term of this patent is extended or adjusted under 35 U.S.C. 154(b) by 0 days.

(21) Appl. No.: 15/535,554

(22) PCT Filed: Dec. 15, 2015

(86) PCT No.: PCT/EP2015/079778
§ 371 (c)(1),
(2) Date: Jun. 13, 2017

(87) PCT Pub. No.: WO2016/096846
PCT Pub. Date: Jun. 23, 2016

(65) Prior Publication Data
US 2017/0327436 A1  Nov. 16, 2017

(30) Foreign Application Priority Data

Dec. 16, 2014  (EP) .................................... 14198129

(51) Int. Cl.
*C07C 2/02* (2006.01)
*B01J 31/22* (2006.01)
*B01J 31/24* (2006.01)
*C07C 11/167* (2006.01)

(52) U.S. Cl.
CPC ................ *C07C 2/02* (2013.01); *B01J 31/22* (2013.01); *B01J 31/2265* (2013.01); *B01J 31/24* (2013.01); *B01J 31/2414* (2013.01); *B01J 2231/546* (2013.01); *B01J 2531/821* (2013.01); *C07C 2531/22* (2013.01); *C07C 2531/24* (2013.01)

(58) Field of Classification Search
CPC ... C07C 2/02; C07C 2531/22; C07C 2531/24; B01J 31/22; B01J 31/24
See application file for complete search history.

(56) References Cited

U.S. PATENT DOCUMENTS

| 2,377,025 A | 5/1945 | Miller |
| 2,420,477 A | 5/1947 | Hale et al. |
| 3,671,604 A | 6/1972 | Rutledge |
| 5,969,170 A | 10/1999 | Grubbs et al. |
| 6,838,489 B2 | 1/2005 | Bell et al. |

(Continued)

OTHER PUBLICATIONS

Trotus et al., "Butadiene from acetylene—ethylene cross-metathesis", : Chem. Commun., 2015, 51, 7124, published Mar. 19, 2015.*

(Continued)

*Primary Examiner* — In Suk C Bullock
*Assistant Examiner* — Ali Z Fadhel
(74) *Attorney, Agent, or Firm* — Norris McLaughlin, P.A.

(57) ABSTRACT

The invention relates to a process for preparing 1,3-butadiene by means of ene-yne metathesis over at least one transition metal catalyst of the element ruthenium.

12 Claims, 1 Drawing Sheet

(56) References Cited

U.S. PATENT DOCUMENTS

| | | | |
|---|---|---|---|
| 6,867,303 | B2 | 3/2005 | Grela |
| 7,750,172 | B2 | 7/2010 | Grubbs et al. |
| 2002/0107138 | A1 | 8/2002 | Hoveyda et al. |
| 2012/0289617 | A1* | 11/2012 | Wang .................. B01J 31/1625 521/33 |
| 2012/0309998 | A1* | 12/2012 | Holtcamp ............ B01J 31/2265 556/20 |

OTHER PUBLICATIONS

Schrock, Richard R. et al., "Molybdenum and Tungsten Imido Alkylidene Complexes as Efficient Olefin-Matathesis Catalysts", Angewandte Chemie, 2003, 42, pp. 4592-4633.

Grela, Karol et al., "A Good Bargain: In Inexpensive, Air-Stable Ruthenium Metathesis Catalyst Derived from α-Asarone", Eur. J. Org. Chem, 2003, Wiley-VCH, pp. 963-966.

Grela, Karol et al., "A Highly Efficient Ruthenium Catalyst for Metathesis Reactions", Angew. Chem. Int. Ed., 2002, Wiley-VCH, 41, No. 21, pp. 4038-4040.

Bujoy, Robert, et al., "Ortho-and Para-Substituted Hoveyda-Grubbs Carbenes. An Improved Synthesis of Highly Efficient Metathesis Initiators", J. Org. Chem., 2004, 69, American Chemical Society, pp. 6894-6896.

Krause, Jens O. et al., "Synthesis and REactivity of Homogeneous and Heterogeneous Ruthenium-Based Metathesis Catalysts Containing Electron-Withdrawing Ligands", Chem. Eur. J. 2004, 10, Wiley-VCH, pp. 777-784.

Schwab, Peter, et al. "Synthesis and Applications of RuCl2(CHR')(PR3)2: The Influence of the Alkylidene Moiety on Metathesis Activity", J. Am. Chem. Soc. 1996, 118, American Chemical Society, pp. 100-110.

International Search Report from International Application No. PCT?EP2015/079778, dated Feb. 11, 2016, two pages.

* cited by examiner

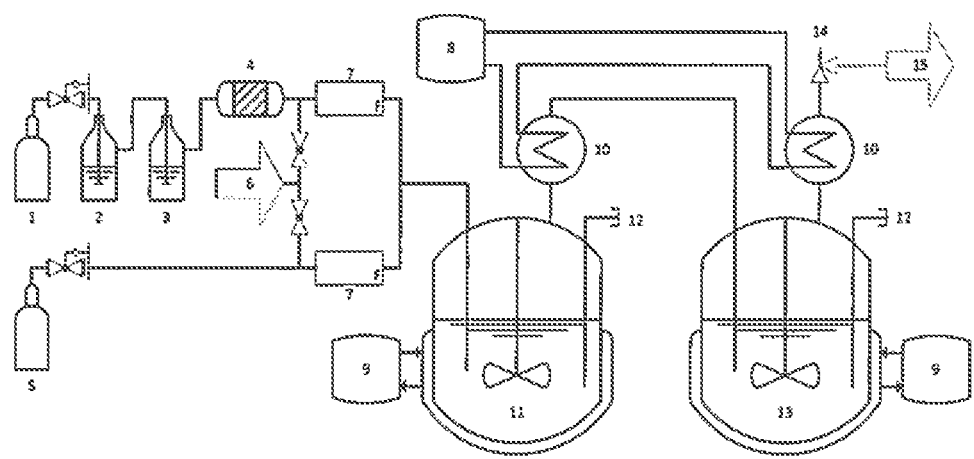

1,3-BUTADIENE SYNTHESIS

This application is a § 371 national stage of PCT International Application No. PCT/EP2015/079778, filed Dec. 15, 2015, which claims foreign priority benefit under 35 U.S.C. § 119 of European Patent Application No. 14198129.0, filed Dec. 16, 2014, the disclosure of each of which is incorporated herein by reference.

The invention relates to a process for preparing 1,3-butadiene by means of ene-yne metathesis over at least one transition metal catalyst of the element ruthenium.

1,3-Butadiene (CAS No. 106-99-0) is usually prepared by thermal dissociation (steam cracking) of saturated hydrocarbons, with naphtha or hydrocarbons in the range from C2 to C4 usually being used as raw material. In the work-up of the mixture formed during cracking, a C4 fraction containing not only 1,3-butadiene but also 1,2-butadiene, n-butane, butenes, 1-butyne, butenyne and propine is obtained.

A disadvantage of isolating 1,3-butadiene from cracker products is that more ethane is always used as cracker raw material at the expense of naphtha. However, the cracking of ethane gives only minimal amounts of 1,3-butadiene, so that the latter is continually becoming scarcer and more expensive. However, an additional main product from cracking processes is ethene.

A further important starting material in the industrial preparation of important basic chemicals is acetylene, also referred to as ethyne, which is prepared industrially by means of high-temperature pyrolysis of light or middle petroleum fractions or natural gas at 2000° C. After the pyrolysis, the gas mixture formed is quickly cooled (quenched) to below 200° C. in order to avoid decomposition of the product into elemental carbon and hydrogen.

U.S. Pat. No. 3,671,604 discloses the catalytic copolymerization of ethyne with monoolefins, wherein acid catalysts from the group consisting of zinc acetate, zinc oxide, cadmium oxide, cadmium acetate, nickel oxide, nickel acetate, cobalt oxide and cobalt acetate are used. The reaction temperatures tested in the process of U.S. Pat. No. 3,671,604 were in the range from 150° C. to 325° C., with only temperatures in the range from 250° C. to 300° C. leading to measurable product yields. The reaction product was a mixture of from thirty to forty components.

Proceeding from this prior art, it was an object of the present invention to provide a process for preparing 1,3-butadiene in a targeted manner from the starting materials ethyne and ethene which are available industrially in large quantities, with the process also proceeding at significantly lower temperatures than in the prior art.

This object is achieved by a process for preparing 1,3-butadiene by reacting ethene and ethyne with one another in the presence of at least one transition metal catalyst of the element ruthenium. This is an ene-yne metathesis.

For clarification, it may be stated that all definitions and parameters mentioned in general terms or in preferred ranges below are encompassed in any combinations by the scope of the present invention.

The invention further relates to the use of transition metal catalysts of the element ruthenium for preparing 1,3-butadiene from ethyne and ethene.

The synthesis according to the invention of 1,3-butadiene from ethyne and ethene is preferably carried out over a homogeneous transition metal catalyst of the element ruthenium.

A feature of homogeneous catalysis is that the reactants or starting materials, the products and the catalyst are present in a single phase within the meaning of the Gibbs phase rule under reaction conditions. This phase can be a gas, a liquid or a supercritical fluid. The catalysts which are the most important by far in homogeneous catalysis and are therefore preferred according to the invention are metal-organic compounds molecularly dissolved in a liquid phase.

For this reason, the 1,3-butadiene synthesis according to the invention is preferably carried out by reacting ethene and ethyne in the liquid phase in the presence of at least one homogeneous transition metal catalyst of the element ruthenium. Here, the at least one transition metal catalyst of the element ruthenium is used in solution. Solvents suitable for the process dissolve the homogeneous catalyst but do not decompose it. As solvent, preference is given to using at least one solvent selected from the group consisting of haloalkanes which are liquid at room temperature, with room temperature meaning 23+/−2° C. Particular preference is given to dichloromethane.

The reaction temperature of the process of the invention is dependent on the decomposition temperature of the catalyst to be used. It can be selected by a person skilled in the art on the basis of routine considerations. In a preferred embodiment, the 1,3-butadiene synthesis according to the invention is therefore carried out at temperatures in the range from −70 to 50° C., particularly preferably in the range from −64 to 45° C., very particularly preferably in the range from −50 to 40° C., in particular in the range from 15 to 40° C. These low temperatures compared to the above-cited prior art make the process of the invention significantly more economical.

The 1,3-butadiene synthesis of the invention is preferably carried out without superatmospheric pressure. This means that, in a preferred embodiment, the process of the invention is carried out at atmospheric pressure of 1013.25 hPa+/−5%.

The synthesis according to the invention of 1,3-butadiene can be carried out both batchwise and continuously. The 1,3-butadiene synthesis of the invention is preferably carried out batchwise. In the batch procedure, the preferred reaction times are in the range from 0.5 to 4 hours, with the reaction time being defined as the total time during which the reaction gases are introduced.

Homogeneous catalysts are often extremely sensitive to oxidation and/or hydrolysis, so that in a preferred embodiment of the process of the invention, the process is carried out under anaerobic conditions, preferably under protective gas. Preference is given to using nitrogen or noble gases, especially nitrogen, as protective gas.

Most metal-organic catalyst complexes are transition metal compounds having a defined structure and stoichiometry. In processes which have been studied exhaustively, the course of the reaction on a molecular basis can be (virtually) completely understood, which is a basis for targeted tailored development of catalysts. The reaction site is typically a metal atom (ion) to which ligands which do not participate directly in the catalysis (spectator ligands, control ligands) are also coordinated. Variations of these ligands from the point of view of exerting a targeted influence on the electronic and/or steric conditions around the reaction site (ligand tuning) are the basis of catalyst optimization in respect of activity, selectivity and stability.

For this reason, preference is given according to the invention to homogeneous transition metal catalysts of the element ruthenium having at least one organic ligand.

As transition metal catalysts to be used according to the invention, preference is given to using those of the general formula (A),

(A)

where
the radicals L are identical or different ligands, preferably uncharged electron donors, or L is an oxygen atom of a substituent R which is coordinated to the ruthenium and
the radicals R are identical or different and are each hydrogen, alkyl, cycloalkyl, alkenyl, alkynyl, aryl, carboxylate, alkoxy, alkenyloxy, alkynyloxy, aryloxy, alkoxycarbonyl, alkylamino, alkylthio, arylthio, alkylsulfonyl or alkylsulfinyl, where these radicals can each optionally be substituted by one or more alkyl, halogen, alkoxy, aryl or heteroaryl radicals, or, as an alternative, the two radicals R are bridged with inclusion of the common carbon atom to which they are bound to form a cyclic group which can be aliphatic or aromatic in nature and is optionally substituted and can contain one or more heteroatoms.

Preference is given to the radicals R in the general formula (A) in each case being, independently of one another, hydrogen, $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{24}$-aryloxy, $C_2$-$C_{20}$-alkoxycarbonyl, $C_1$-$C_{30}$-alkylamino, $C_1$-$C_{30}$-alkylthio, $C_6$-$C_{24}$-arylthio, $C_1$-$C_{20}$-alkylsulfonyl or $C_1$-$C_{20}$-alkylsulfinyl, where these radicals can in each case optionally be substituted by one or more $C_1$-$C_6$-alkyl, halogen, $C_1$-$C_6$-alkoxy, preferably i-propoxy, aryl or heteroaryl radicals, or, as an alternative, the two radicals R are bridged with inclusion of the common carbon atom to which they are bound to form a cyclic group which can be aliphatic or aromatic in nature and is optionally substituted and can contain one or more heteroatoms.

In a preferred embodiment, the two ligands L can each be, independently of one another, a phosphine, sulfonated phosphine, phosphate, phosphinite, phosphonite, ether, amine, amide, sulfoxide, carboxyl, nitrosyl, pyridine, thioether or imidazolidine ("Im") ligand.

Preference is given to the two ligands L each being, independently of one another, a $C_6$-$C_{24}$-arylphosphine, $C_1$-$C_{10}$-alkylphosphine or $C_3$-$C_{20}$-cycloalkylphosphine ligand, a sulfonated $C_6$-$C_{24}$-arylphosphine or sulfonated $C_1$-$C_{10}$-alkylphosphine ligand, a $C_6$-$C_3$-arylphosphinite or $C_1$-$C_{10}$-alkylphosphinite ligand, a $C_6$-$C_{14}$-arylphosphonite or $C_1$-$C_{10}$-alkylphosphonite ligand, a $C_6$-$C_{24}$-arylphosphite or $C_1$-$C_{10}$-alkylphosphite ligand, a $C_6$-$C_{24}$-arylarsine or $C_1$-$C_{10}$-alkylarsine ligand, a $C_6$-$C_{24}$-arylamine or $C_1$-$C_{10}$-alkylamine ligand, a pyridine ligand, a $C_6$-$C_{24}$-aryl sulfoxide or $C_1$-$C_{10}$-alkyl sulfoxide ligand, a $C_6$-$C_{24}$-aryl ether or $C_1$-$C_{10}$-alkyl ether ligand or a $C_6$-$C_{24}$-arylamide or $C_1$-$C_{10}$-alkylamide ligand, each of which can be substituted by a phenyl group which in turn is optionally substituted by a halogen, $C_1$-$C_5$-alkyl or $C_1$-$C_5$-alkoxy radical, or L is an oxygen atom of a substituent R which is coordinated to the ruthenium.

The term "phosphine" encompasses, in particular, $PPh_3$, $P(p-Tol)_3$, $P(o-Tol)_3$, $PPh(CH_3)_2$, $P(CF_3)_3$, $P(p-FC_6H_4)_3$, $P(p-CF_3C_6H_4)_3$, $P(C_6H_4$—$SO_3Na)_3$, $P(CH_2C_6H_4$—$SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ and $P(neophenyl)_3$.

For the purposes of the present invention, "alkyl" denotes a straight-chain or branched saturated hydrocarbon group. In some embodiments, an alkyl group having from 1 to 6 carbon atoms is used and can be referred to as a "lower alkyl group". Preferred alkyl groups are methyl (Me), ethyl (Et), propyl, in particular n-propyl and isopropyl, butyl, in particular n-butyl, isobutyl, sec-butyl, tert-butyl, pentyl groups, in particular n-pentyl, isopentyl, neopentyl, hexyl groups and the like.

For the purposes of the present invention. "aryl" denotes a monocyclic aromatic hydrocarbon ring system or a polycyclic ring system in which two or more aromatic hydrocarbon rings are fused, or at least one aromatic monocyclic hydrocarbon ring which is fused with one or more cycloalkyl and/or cycloheteroalkyl rings. An aryl group can have from 6 to 24 carbon atoms in its ring system, for example a $C_{6-20}$-aryl group, and contain a plurality of fused rings. In some embodiments, aryl or arylene can be a polycyclic aryl group having from 8 to 24 carbon atoms. Preferred aryl groups having an aromatic carbocyclic ring system are phenyl, 1-naphthyl (bicyclic), 2-naphthyl (bicyclic), anthracenyl (tricyclic), phenanthrenyl (tricyclic), pentacenyl (penta) and similar groups. Other preferred aryl groups are benzodioxanyl, benzodioxolyl, chromanyl, indolinyl groups and the like. In some embodiments, aryl groups, in particular phenyl groups, can, as described herein, be substituted, in particular by an i-propoxy radical. In some embodiments, an aryl group can have one or more substituents. Particular preference is given to aryl being phenyl.

For the purposes of the present invention, "cycloalkyl" denotes a nonaromatic carbocyclic group containing cyclized alkyl, alkenyl or alkynyl groups. In various embodiments, a cycloalkyl group contains from 3 to 24 carbon atoms, preferably from 3 to 20 carbon atoms, e.g. a $C_{3-14}$-cycloalkyl group. A cycloalkyl group can be monocyclic, for example cyclohexyl, or else be polycyclic, as in, for example, bridged and/or spiro ring systems, with the carbon atoms being able to be present within or outside the ring system. Each suitable ring position of the cycloalkyl group can be covalently bound to the defined chemical structure. Preferred cycloalkyl groups are cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl and spiro[4.5]decanyl groups and also their homologs, isomers and the like. In some embodiments, the cycloalkyl groups can be substituted. Preference is given according to the invention to unsubstituted cycloalkyl groups.

For the purposes of the present invention, "arylalkyl" denotes an alkyl-aryl group, with the arylalkyl group being covalently bound to the defined chemical structure via the alkyl group. An arylalkyl group which is preferred according to the invention is the benzyl group (—$CH_2$—$C_5H_5$). Arylalkyl groups according to the present invention can optionally be substituted, i.e. either the aryl group and/or the alkyl group can be substituted.

The term "phosphinite" encompasses, for example, triphenyl phosphinite, tricyclohexyl phosphinite, triisopropyl phosphinite and methyl diphenylphosphinite.

The term "phosphite" encompasses, in particular, triphenyl phosphite, tricyclohexyl phosphite, tri-tert-butyl phosphite, triisopropyl phosphite and methyl diphenyl phosphite.

The term "sulfonate" encompasses, in particular, trifluoromethanesulfonate, tosylate and mesylate.

The term "sulfoxide" encompasses, in particular, $(CH_3)_2S(=O)$ and $(C_6H_5)_2S=O$.

The term "thioether" encompasses, in particular, $CH_3SCH_3$, $C_6H_5SCH_3$, $CH_3OCH_2CH_2SCH_3$ and tetrahydrothiophene.

For the purposes of the present patent application, the term "pyridine" is intended as collective term for all nitrogen-containing ligands as are mentioned, for example, by Grubbs in WO-A-03/011455. Examples are: pyridine, picolines (α-, β-, and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino)pyridine, chloropyridines, bromopyridines, nitropyridines, quinoline, pyrimidine, pyrrole, imidazole and phenylimidazole.

If one or both of the ligands L in formula (A) is an imidazolidine radical (Im), this usually has a structure of the general formulae (IIa) or (IIb),

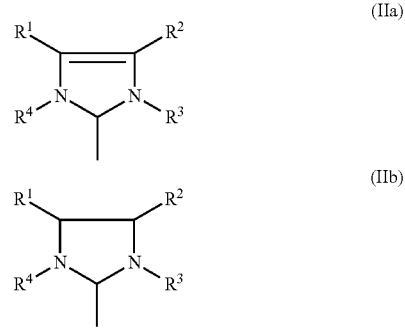

where $R^1$, $R^2$, $R^3$, $R^4$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulfonyl, $C_1$-$C_{20}$-alkylsulfonate, $C_6$-$C_{20}$-arylsulfonate or $C_1$-$C_{20}$-alkylsulfinyl.

One or more of the radicals $R^1$, $R^2$, $R^3$, $R^4$ can, independently of one another, optionally be substituted by one or more substituents, preferably straight-chain or branched $C_1$-$C_{10}$-alkyl, $C_3$-$C_8$-cycloalkyl, $C_1$-$C_{10}$-alkoxy or $C_6$-$C_{24}$-aryl, with these abovementioned substituents in turn being able to be substituted by one or more radicals, preferably selected from the group consisting of halogen, in particular chlorine or bromine, $C_1$-$C_5$-alkyl, $C_1$-$C_5$-alkoxy and phenyl.

Merely for the purposes of clarification, it may be added that the structures of the imidazolidine radical depicted in the general formulae (IIa) and (IIb) are equivalent to the structures depicted in the literature for this imidazolidine radical (Im) which emphasize the carbene character of the imidazolidine radical. This also applies analogously to the associated preferred structures (IIIa)-(IIIf) depicted below.

In a preferred embodiment of the catalysts of the general formula (A) having at least one imidazolidine radical (Im) as ligand L, $R^1$ and $R^2$ are each, independently of one another, hydrogen, $C_6$-$C_4$-aryl, particularly preferably phenyl, straight-chain or branched $C_1$-$C_{10}$-alkyl, particularly preferably propyl or butyl, or together form, with inclusion of the carbon atoms to which they are bound, a cycloalkyl or aryl radical, with all the abovementioned radicals optionally being able to in turn be substituted by one or more further radicals selected from the group consisting of straight-chain or branched $C_1$-$C_{10}$-alkyl, $C_1$-$C_{10}$-alkoxy, $C_6$-$C_{24}$-aryl and a functional group selected from the group consisting of hydroxy, thiol, thioether, ketone, aldehyde, ester, ether, amine, imine, amide, nitro, carboxylic acid, disulfide, carbonate, isocyanate, carbodiimide, carboalkoxy, carbamate and halogen.

In a preferred embodiment of the catalysts of the general formula (A) having at least one imidazolidine radical (Im) as ligand L, the radicals $R^3$ and $R^4$ are identical or different and are each straight-chain or branched $C_1$-$C_{10}$-alkyl, particularly preferably i-propyl or neopentyl, $C_3$-$C_{10}$-cycloalkyl, preferably adamantyl, $C_6$-$C_{24}$-aryl, particularly preferably phenyl, $C_1$-$C_{10}$-alkylsulfonate, particularly preferably methanesulfonate, $C_6$-$C_{10}$-arylsulfonate, particularly preferably p-toluenesulfonate.

The abovementioned radicals as meanings of $R^3$ and $R^4$ are optionally substituted by one or more further radicals selected from the group consisting of straight-chain or branched $C_1$-$C_5$-alkyl, in particular methyl, $C_1$-$C_5$-alkoxy, aryl and a functional group selected from the group consisting of hydroxy, thiol, thioether, ketone, aldehyde, ester, ether, amine, imine, amide, nitro, carboxylic acid, disulfide, carbonate, isocyanate, carbodiimide, carboalkoxy, carbamate and halogen.

In particular, the radicals $R^3$ and $R^4$ can be identical or different and each be i-propyl, neopentyl, adamantyl, mesityl or 2,6-diisopropylphenyl.

Particularly preferred imidazolidine radicals (Im) in the ligand L have the following structures (IIa) to (IIIf), where Ph is in each case a phenyl radical, Bu is a butyl radical and Mes is in each case a 2,4,6-trimethylphenyl radical or Mes is, as an alternative, 2,6-diisopropylphenyl in all cases.

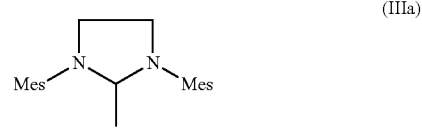

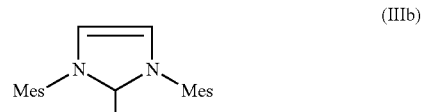

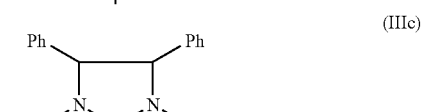

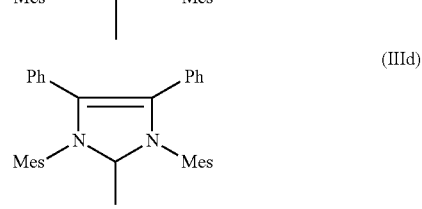

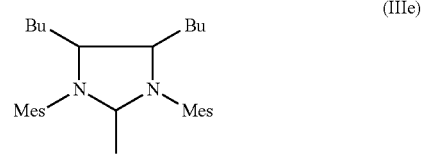

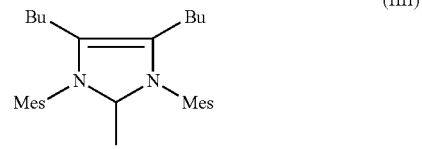

A variety of representatives of the catalysts of the formula (A) are known in principle, for example from WO-A-96/04289 and WO-A-97/06185.

As an alternative to the preferred Im radicals, one or both of the ligands L in the general formula (A) are preferably also identical or different trialkylphosphine ligands, where at least one of the alkyl groups is a secondary alkyl group or a cycloalkyl group, preferably isopropyl, isobutyl, sec-butyl, neopentyl, cyclopentyl or cyclohexyl.

One or both ligands L in the general formula (A) are particularly a trialkylphosphine ligand, where at least one of the alkyl groups is a secondary alkyl group or a cycloalkyl group, preferably isopropyl, isoburyl, sec-butyl, neopentyl, cyclopentyl or cyclohexyl.

In a preferred embodiment, ruthenium-based transition metal catalysts of the formula (B) are used,

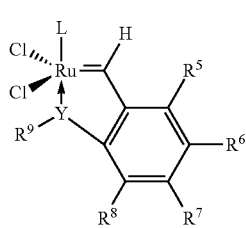

(B)

where

Y is oxygen (O) or sulfur (S), preferably oxygen, $R^5$, $R^6$, $R^7$ and $R^8$ are identical or different and are each hydrogen, organic or inorganic radicals, preferably hydrogen or —$SO_2$—$N(CH_3)_2$ or —NH—CO—$CF_3$, $R^9$ is an alkyl, cycloalkyl, alkenyl, alkynyl, aryl, alkoxy, alkenyloxy, alkynyloxy, aryloxy, alkoxycarbonyl, alkylamino, alkylthio, arylthio, alkylsulfonyl or alkylsulfinyl radical, preferably i-propyl, each of which can optionally be substituted by one or more alkyl, halogen, alkoxy, aryl or heteroaryl radicals, and L is a ligand which has the same meanings as indicated for the formula (A).

The catalysts of the formula (B) are known in principle. Representatives of this class of compounds are the catalysts described by Hoveyda et al. in US 2002/0107138 A1 and Angew. Chem. Int. Ed. 2003, 42, 4592 and the catalysts described by Grela in WO-A-2004/035596, Eur. J. Org. Chem 2003, 963-966 and Angew. Chem. Int. Ed. 2002, 41, 4038 and in J. Org. Chem. 2004, 69, 6894-96 and Chem. Eur. J 2004, 10, 777-784. The catalysts of the formula (B) are commercially available or can be prepared according to the literature references indicated.

As particularly preferred ruthenium transition metal catalyst, at least one catalyst from the group M1=benzylidene[1,3-bis(2,4,6-trimethylphenyl)-2-imidazolidinylidene]dichloro(tricyclohexylphosphine)ruthenium (Grubbs II catalyst, CAS No. 246047-72-3), M2=bis(tricyclohexylphosphine)[(phenylthio)methylene]ruthenium(II) dichloride (CAS No. 219770-99-7), M3=1,3-bis(2,4,6-trimethylphenyl)-4,5-dihydroimidazol-2-ylidene[2-(i-propoxy)-5-(N,N-di-MeNH$_2$SO$_2$)phenyl]methyleneruthenium(II) dichloride (Zhan Cat. 1B, CAS No. 918870-76-5), M4=bis(tricyclohexylphosphine)-3-phenyl-1H-inden-1-ylideneruthenium(II) dichloride (CAS No. 250220-36-1), M5=benzylidenebis(tricyclohexylphosphine)dichlororuthenium (Grubbs I catalyst, CAS No. 172222-30-9), M6=dichloro(o-isopropoxyphenylmethylene)-(tricyclohexylphosphine)ruthenium(II) (Hoveyda-Grubbs Cat. I, CAS No. 203714-71-0), M7=(1,3-bis(2,4,6-trimethylphenyl)-2-imidazolidinylidene) dichloro(o-isopropoxyphenyl methylene)ruthenium (Hoveyda-Grubbs Cat. II, CAS No. 301224-40-8), M8=tricyclohexylphosphine[4,5-dimethyl-1,3-bis(2,4,6-trimethylphenyl)imidazol-2-ylidene][2-thienylmethylene]ruthenium(II) dichloride, at least 95% (CAS No. 1190427-50-9), M9=tricyclohexylphosphine[1,3-bis(2,4,6-trimethylphenyl)imidazol-2-ylidene][3-phenyl-1H-inden-1-ylidene]ruthenium(II) dichloride, at least 95% (CAS No. 254972-49-1), M10=[1,3-bis(2,6-di-i-propylphenyl)-4,5-dihydroimidazol-2-ylidene]-[2-i-propoxy-5-(trifluoroacetamido)phenyl]methyleneruthenium(II) dichloride (CAS No. 1212008-99-5), M11=tri(i-propoxy)phosphine(3-phenyl-1H-inden-1-ylidene)[1,3-bis(2,4,6-trimethyl phenyl)-4,5-dihydroimidazol-2-ylidene]ruthenium(II) dichloride, at least 95% (Strem Chemicals catalog number 44-7783), M12=tricyclohexylphosphine[1,3-bis(2,4,6-trimethylphenyl)imidazol-2-ylidene][2-thienyl methylene]ruthenium (II) dichloride, at least 95% (CAS No. 1190427-49-6), M13=3-phenyl-1H-inden-1-ylidene[bis(i-butylphobane)]ruthenium(II) dichloride (CAS No. 894423-99-5), M14=dichloro[1,3-bis(2-methylphenyl)-2-imidazolindinylidene](benzylidene) (tricyclohexyl phosphine)ruthenium(II) (CAS No. 927429-60-5), M15=dichloro[1,3-bis(2-methylphenyl)-2-imidazolindinylidene](2-isopropoxyphenyl methylene)ruthenium(II) (CAS No. 927429-61-6)

is used in the 1,3-butadiene synthesis of the invention. Particular preference is given to using M5 as transition metal catalyst of the element ruthenium.

The preparation of the catalysts to be used according to the invention is known to those skilled in the art. Examples may be found in P. Schwab, R. H. Grubbs, J. W. Ziller, *J. Am. Chem. Soc.,* 1996, 118 (I), p. 100-110. In addition, the catalysts M1 to MlS are commercially available from Sigma-Aldrich Laborchemikalien GmbH, Seelze, Germany or Strem Chemicals Inc. Kehl, Germany.

The amount of the transition metal catalysts of the element ruthenium to be used according to the invention in the reaction mixture is usually in the range from 0.01 to 10 000 mol %, preferably from 0.1 to 100 mol %, particularly preferably from 0.2 to mol %, calculated as the sum of all catalysts to be used and based on the amount of ethene used.

The total gas flow, i.e. the mixture of ethene and ethyne which is to be fed as starting material to the reaction apparatus, is preferably in the range from 200 to 500/h, particularly preferably in the range from 200 to 400 l/h, very particularly preferably in the range from 200 to 300 l/h, at a solvent volume of 1l. A person skilled in the art can calculate the corresponding parameters for smaller or larger batches on the basis of these figures.

In the total gas flow, the starting materials ethene and ethyne are preferably present in a ratio in the range from 6:4 to 4:6, particularly preferably in a ratio in the region of 1:1.

In a preferred embodiment, the gas stream containing the mixture of ethene and ethyne is dried before entering the reaction apparatus. Suitable desiccants are known to those skilled in the art. Preference is given to using at least one desiccant from the group consisting of concentrated sulfuric acid, sodium hydroxide and molecular sieves for drying the gas mixture to be used according to the invention. In particular, all three desiccants are used in succession.

Any type of reaction vessel or apparatus which is usually used by a person skilled in the art for the reaction of gases is suitable for the 1,3-butadiene synthesis of the invention. Preference is given to stirred tank reactors, flow tubes or bubble column reactors. These are preferably made of steel. For relatively small batches, glass-based reactors can also be used. The terms reaction vessel, apparatus and reactor are used synonymously in the present patent application.

In general, the reaction is carried out by introducing the at least one transition metal catalyst of the element ruthenium, in the case of a catalyst mixture optionally in premixed form, as such or preferably as a solution in at least one of the abovementioned solvents, optionally with cooling but under protective gas, in particular nitrogen, into at least one cooled reaction vessel.

The at least one reaction vessel is preferably maintained at temperatures in the range from −70 to 50° C., particularly preferably at temperatures in the range from 15 to 40° C. A mixture of purified ethyne and ethene is introduced through an inlet, preferably below the liquid level when solvents are used.

The unreacted proportion of the gas mixture can either be fed back into the reaction vessel or, in an alternative embodiment, be transferred into at least one second reaction vessel which likewise contains at least one transition metal catalyst of the element ruthenium to be used according to the invention. Here too, the introduction of the starting mixture of ethene and ethyne is effected underneath the surface of the liquid if solvents are used. Unreacted gas mixture leaving this vessel can either be fed back into the first reaction vessel or be fed back into the at least one second reaction vessel, or be discharged into the surrounding air/exhaust air.

The handling of ethyne is demanding from a safety point of view, especially under superatmospheric pressure, which is why the gas mixture containing the starting materials is preferably passed through the catalyst-containing solvent at only a small superatmospheric pressure of up to 100 mbar gauge.

With a boiling point of −4.5° C., 1,3-butadiene accumulates in the solvent and can be separated off by distillation from this and by-products formed. The termination of the synthesis according to the invention of 1,3-butadiene from ethene and ethyne and the purification of the reaction products can be carried out by methods generally known to those skilled in the art. The solvent can also be used, after reaction products have been separated off, to make the at least one catalyst available to the reaction again.

EXAMPLES

Starting Materials
Ethene, CAS No. 74-85-1, purity 99.9%, procured from Linde AG
Ethyne, CAS No. 74-86-2, purity 99.5%, procured from Linde AG
Catalysts: M1 to M15 as per the description from Sigma-Aldrich Laborchemikalien GmbH, Seelze, Germany or Strem Chemicals Inc. Kehl, Germany
Protective gas: nitrogen

APPARATUS

FIG. 1 shows, by way of example, an apparatus as was used for the experiments within the framework of the present invention. The reference numerals in FIG. 1 have the following meanings:

1 ethyne
2 $H_2SO_4$ (95%-98%)
3 2 N NaOH
4 molecular sieve 4 Å (Sigma Aldrich)
5 ethene
6 protective gas $N_2$
7 bubble counter
8 cryostat −20° C.
9 heating bath
10 low-temperature cooler
11 reactor 1, 250 ml, glass
12 septum
13 reactor 2, 250 ml, glass
14 about 100 mbar gauge
exhaust air The experimental apparatus consisted of two reactors (250 ml three-necked glass flask) provided with magnetic stirrer bar, two low-temperature coolers (cooling liquid maintained at −20° C.), two septi for sampling and two oil baths as heating bath. The gas mixture composed of previously purified ethyne (first 95-98% strength $H_2SO_4$ then 2 N NaOH and finally molecular sieve) and ethene was firstly introduced into a first reactor below the surface of the liquid via a glass capillary having a diameter in the range from 1.5 to 7 mm. The proportion of this gas mixture which was not consumed by the reaction or condensed in the low-temperature cooler of reactor 1 was in turn conveyed via a further capillary into a second reactor underneath the surface of the liquid. After passage through the second low-temperature cooler, the proportions of the gas mixture which had not been reacted or not condensed in the low-temperature cooler of reactor 2 went into the exhaust air.

The liquid contents of reactor 1 and reactor 2 were analyzed by means of GC (gas chromatography). Owing to the low conversions, the evaluation was only qualitative. However, the presence of the reference substance cyclohexane allowed the amount of butadiene formed to be compared by means of the peak area ratio of butadiene to cyclohexane for the experiments within the framework of the present invention.

Table 1 shows the substances found with their respective retention times. Identification was effected by comparison with commercial pure substances or by means of GC-MS (MS=mass spectrometry).

TABLE 1

| Retention time/min | Substance |
|---|---|
| 2.08 | ethene, ethyne, air |
| 2.26 | 1,3-butadiene |
| 2.69 | trans-1,3-pentadiene |
| 2.75 | cis-1,3-pentadiene |
| 2.88 | dichloromethane |
| 3.64 | cyclohexane |
| 4.14; 4.35; 4.37 | 2,4-hexadiene isomers |
| 4.70 | benzene |
| 7.01 | toluene |
| 8.94 | octatetraene |
| 9.25 | styrene |

Comparative Example 1 (without Catalyst)

50 ml of dichloromethane were brought to 30° C. under protective gas in a 100 ml glass vessel filled with low-temperature cooler (temperature of the cooling medium −20° C.) which had previously been made inert by means of $N_2$. Making spaces inert refers to the procedure of displacing the atmospheric oxygen or reactive or explosive gases or gas mixtures from spaces by introduction of inert gases or vapors. In addition, 1.0 ml of cyclohexane was added as reference to the dichloromethane. A mixture of ethene and ethyne in a ratio of 1:1 was subsequently passed into the solvent while stirring during the entire reaction time, with samples being taken from the liquid phase at regular intervals. No butadiene was formed.

Comparative Example 2 (M4, without Ethene)

50 mg of catalyst M4, dissolved in 50 ml of dichloromethane, were brought to 30° C. under protective gas in a vessel with low-temperature cooler (temperature of the cooling medium −20° C.) which had previously been made inert by means of $N_2$. In addition, 1.0 ml of cyclohexane were added as reference. Ethyne was subsequently introduced while stirring during the entire reaction time and samples were taken from the liquid phase at regular intervals. No butadiene was formed.

Comparative Example 3 (M5, Without Ethene)

50 mg of catalyst M5, dissolved in 50 ml of dichloromethane, were brought to 30° C. under protective gas in a vessel with low-temperature cooler (temperature of the cooling medium −20° C.) which had previously been made inert. In addition, 1.0 ml of cyclohexane were added as reference. Ethyne was subsequently introduced while stirring during the entire reaction time and samples were taken from the liquid phase at regular intervals. No butadiene was formed.

Example 1

50 mg of catalyst MX, where MX is in each case one of the abovementioned catalysts M1 to M15, dissolved in 50 ml of dichloromethane, were brought to 30° C. under protective gas ($N_2$) in a vessel with low-temperature cooler (temperature of the cooling medium −20° C.) which had previously been made inert by means of $N_2$. In addition, 1.0 ml of cyclohexane were added as reference. A mixture of ethene and ethyne in a ratio of 1:1 was subsequently introduced into the solvent underneath the surface of the liquid while stirring during the entire reaction time. Samples were taken from the liquid phase at regular intervals during the reaction time. Butadiene was detected by gas chromatography in these samples.

Example 2 (M5, −64° C.)

50 mg of catalyst M5, dissolved in 50 ml of dichloromethane, were brought to −64° C. under protective gas in a vessel with low-temperature cooler (temperature of the cooling medium −20° C.) which had previously been made inert by means of $N_2$. In addition, 1.0 ml of cyclohexane was added as reference. A mixture of ethene and ethyne in a ratio of 1:1 was subsequently introduced while stirring during the entire reaction time. Samples were taken from the liquid phase at regular intervals during the reaction time. Butadiene was detected by gas chromatography in these samples.

Example 3 (M5, Double the Amount of Catalyst)

100 mg of catalyst M5, dissolved in 50 ml of dichloromethane, were brought to 30° C. under protective gas ($N_2$) in a vessel with low-temperature cooler (temperature of the cooling medium −20° C.) which had previously been made inert by means of $N_2$. In addition, 1.0 ml of cyclohexane was added as reference. A mixture of ethene and ethyne in a ratio of 1:1 was subsequently introduced while stirring during the entire reaction time. Samples were taken from the liquid phase at regular intervals during the reaction time. Butadiene was detected by gas chromatography in these samples.

Comparative examples 1 to 3 show that two components are essential for carrying out the process of the invention: ethyne has to be contacted firstly with catalyst and secondly with ethene.

What is claimed is:

1. A process for preparing 1,3-butadiene, the process comprising contacting ethene and ethyne in the presence of at least one transition metal catalyst selected from the group consisting of:
   M1=benzylidene[1,3-bis(2,4,6-trimethyphenyl)-2-imidazolidinylidene]dichloro(tricyclohexylphosphine)ruthenium,
   M2=bis(tricyclohexylphosphine)[(phenylthio)methylene]ruthenium(II) dichloride,
   M3=1,3-bis(2,4,6-trimethylphenyl)-4,5-dihydroimidazol-2-ylidene[2-(i-propoxy)-5-(N,N-di-MeNH$_2$SO$_2$)phenyl]methyleneruthenium(II) dichloride,
   M4=bis(tricyclohexylphosphine)-3-phenyl-1H-inden-1-ylideneruthenium(II) dichloride,
   M5=benzylidenebis(tricyclohexylphosphine)dichlororuthenium,
   M6=dichloro(o-isopropoxyphenylmetnylene)-(tricyclohexylphosphine)ruthenium(II),
   M7=(1,3)-bis(2,4,6-trimethylphenyl-2-imidazolidinylidene)dichloro(o-isopropoxyphenyl methylene)ruthenium,
   M8=tricyclohexylphosphine[4,5-dimethyl-1,3-bis(2,4,6-trimethylphenyl)imidazol-2-yldene][2-thlenylmethylene]ruthenium(II) dichloride,
   M9=tricyclohexylphosphine[1,3-bis(2,4,6-trimethylphenyl)imidazol-2-ylidene][3-phenyl-1H-inden-1-ylidene]ruthenium(II) dichloride,
   M10=[1,3-bis)(2,6-dl-i-propylphenyl)-4,5-dihydroimidazol-2-ylidene]-[2-i-propoxy-5-(trifluoroacetamido)phenyl]methyleneruthenium(II) dichloride,
   M11=tri(i-propoxy)phosphine(3-phenyl-1H-inden-1-ylidene)[1,3-bis(2,4,6-trimethyl phenyl)-4,5-dihydroimidazol-2-ylidene]ruthenium(II) dichloride,
   M12=tricyclohexylphosphine[1,3-bis(2,4,6-trirmethylphenyl)imidazol-2-ylidene][2-thienyl methylene]ruthenium(II) dichloride,
   M13=3-phenyl-1H-inden-1-ylidene[bis(i-butylphobane)]ruthenium(II) dichloride,
   M14=dichloro[1,3-bis(2-methylphenyl)-2-imidazolindinylidene](benzylidene) (tricyclohexyl phosphine)ruthenium(II), and
   M15=dichloro[1,3-bis(2-methylphenyl)-2-imidazolindinylidene](2-isopropoxyphenyl methylene)ruthenium(II).

2. The process as claimed in claim 1, wherein the contacting is carried out in liquid phase using at least one solvent.

3. The process as claimed in claim 2, wherein the solvent is a haloalkane which is liquid at room temperature.

4. The process as claimed in claim 1, wherein the contacting is carried out at a temperature of −70 to 50° C.

5. The process as claimed in claim 1, wherein the contacting is carried out without superatmospheric pressure.

6. The process as claimed in claim 1, wherein the at least one transition metal catalyst comprises at least M5.

7. The process as claimed in claim 1, wherein the at least one catalyst is present in the reaction mixture in an amount of 0.01 to 10,000 mol %, calculated as sum of all catalysts used and based on the amount of ethane used.

8. The process as claimed in claim 1, wherein the process is carried out batchwise.

9. The process a claimed in claim 2, wherein the ethene and ethyne are in the form of a gas mixture at a ratio of 6:4 to 4:6, and are fed as a gas stream into contact with the liquid phase of catalyst and solvent.

10. The process as claimed in claim 1, wherein:
- the contacting is carried out in liquid phase using at least one advent in which the catalyst is soluble and which is liquid at room temperature;
- the contacting is carried out at ambient pressure and a temperature of −70 to 50° C.; and
- the ethane and ethyne are in the form of a gas mixture at a ratio of 6:4 to 4:6, and are fed as a gas stream into contact with the liquid phase of catalyst and solvent.

11. The process a claimed in claim 2, wherein the solvent is dichloromethane.

12. The process as claimed in claim 10, wherein the solvent is dichloromethane.

\* \* \* \* \*